US008183018B2

(12) United States Patent
Haering et al.

(10) Patent No.: US 8,183,018 B2
(45) Date of Patent: May 22, 2012

(54) PROCESS FOR PRODUCING OF EPOXY-CONTAINING (METH)ACRYLIC ESTERS, USING LIPASES

(75) Inventors: Dietmar Haering, Neu-Edingen (DE); Uwe Meisenburg, Mannheim (DE); Mathieu Chabanas, Berg (DE); Gunter Lipowsky, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 414 days.

(21) Appl. No.: 12/442,967

(22) PCT Filed: Oct. 23, 2007

(86) PCT No.: PCT/EP2007/061304
§ 371 (c)(1),
(2), (4) Date: Mar. 26, 2009

(87) PCT Pub. No.: WO2008/049814
PCT Pub. Date: May 2, 2008

(65) Prior Publication Data
US 2010/0048927 A1    Feb. 25, 2010

(30) Foreign Application Priority Data
Oct. 26, 2006   (EP) ..................................... 06123028

(51) Int. Cl.
*C12P 17/00* (2006.01)
(52) U.S. Cl. .......................... 435/117; 435/123; 435/198
(58) Field of Classification Search .................. 435/117, 435/123, 198
See application file for complete search history.

(56) References Cited

U.S. PATENT DOCUMENTS

| 2,556,075 A | 6/1951 | Erickson |
| 2,680,109 A | 6/1954 | Stevens |
| 2006/0148975 A1 | 7/2006 | Rink et al. |
| 2006/0189823 A1 | 8/2006 | Weikard et al. |

FOREIGN PATENT DOCUMENTS

| EP | 1 693 359 | 8/2006 |
| JP | 2004 331506 | 11/2004 |
| WO | 2004 042069 | 5/2004 |

OTHER PUBLICATIONS

Strietwieser et al. "Introduction to Orgnaic Chemistry" (1981) (Macmillan Publishing Co, Inc.: New York), pp. 266 and 516-518).*
Xin, D. et al., "Synthesis of Glycidyl Acrylate in Organic Solvents Catalyzed by Lipase", Sen'i Gakkaishi, vol. 52, No. 10, pp. 524-528 (1996).
Gladkikh, A. F. et al., "Synthesis of 2-(Glycidyloxy) Ethyl Acrylate and Methacrylate", J. Org. Chem., pp. 1602-1604 (1975).
Fuller, C. W. et al., "Covalent Immobilization of Soluble and Enzymically Active Adenine Nucleotide Coenzymes by a Single Step Procedure", The Journal of Biological Chemistry, vol. 252, No. 19, pp. 6631-6639 (1977).
U.S. Appl. No. 12/743,819, filed May 20, 2010, Haering, et al.

* cited by examiner

*Primary Examiner* — Susan Hanley
(74) *Attorney, Agent, or Firm* — Oblon, Spivak, McClelland, Maier & Neustadt, L.L.P.

(57) ABSTRACT

A process for preparing (meth)acrylic esters (F) of alcohols (A) having at least one epoxy group, in which at least one alcohol (A) having at least one epoxy group is esterified with (meth)acrylic acid (S) or is transesterified with at least one (meth)acrylic ester (D) in the presence of at least one enzyme, the alcoholic leaving group being stable under the reaction conditions in the case of the transesterification.

9 Claims, No Drawings

PROCESS FOR PRODUCING OF EPOXY-CONTAINING (METH)ACRYLIC ESTERS, USING LIPASES

The present invention relates to a process for preparing (meth)acrylic esters comprising epoxy groups and to their use.

In the context of the present invention, (meth)acrylic acid is understood to mean acrylic acid and/or methacrylic acid; (meth)acrylic ester is understood to mean acrylic ester and/or methacrylic ester.

(Meth)acrylic esters are usually prepared by acid- or base-catalyzed esterification of (meth)acrylic acid or by transesterification of other (meth)acrylic esters with alcohols.

(Meth)acrylic esters of alcohols comprising epoxy groups are known in principle. Such esters find use, for example, in polymer dispersions for coatings U.S. Pat. No. 2,680,109 describes the preparation of polymers from monomers which comprise at least one 1,2-epoxy group. In Example 1, glycidyl methacrylate was synthesized from methacryloyl chloride and glycidol in the presence of pyridine in benzene. After distillation, a pure product was obtained with unknown yield.

U.S. Pat. No. 2,556,075 likewise describes a process for preparing polymers with glycidyl units. According to this, glycidyl (meth)acrylate was synthesized from potassium (meth)acrylate and epichlorohydrin at 118° C. for 23 hours. The pure product was obtained in unknown yield after distillation.

Gladkikh et al. disclose, in J. Org. Chem. USSR, 1975, 11, 1602-1604, the preparation of (2-glycidyloxy)ethyl acrylate from hydroxyethyl acrylate and epichlorohydrin in benzene with boron trifluoride at 70° C. and a reaction time of one hour. After purification, (extraction, distillation and reaction of the chlorinate impurities), a pure product was obtained with 40% yield.

In J. Biol. Chem., 1977, 252, 6631-6639, Fuller et al. describe the synthesis of (butanediol glycidyl glyceryl ether) acrylate by addition of acrylic acid to butanediol diglycidyl ether. The brownish material formed had a purity of 80% and was used further for the polymerization.

JP 2004334506 discloses the synthesis of epoxy-terminated (meth)acrylates by transesterifying methacrylate with epoxy-terminated alcohols with titanium catalysts, for example Ti(OBu)$_4$. After extraction with toluene and subsequent distillation, the product was obtained with a yield of 83% in a purity of 99.5%.

A process and the preparation of hydroxyalkyl (meth)acrylates starting from alcohols having epoxy groups is likewise described in EP 1 693 359 A1. The conversion of the alcohols is effected in the presence of Lewis acids which each bear at least one directly bonded di(cyclo)alkylamino group.

A factor common to all of the synthesis processes mentioned is that the (meth)acrylic ester comprising epoxy groups is obtained by a conventionally chemical route.

Xin et al. described, in Seni Gakkaishi 1996, 52 (1), 524-528, the lipase-catalyzed synthesis of glycidyl acrylate from glycidol and vinyl acrylate for the first time. In this study, the influence of three different lipases, four solvents and polymeric additives on the conversion was examined. Quantitative conversions were not described, since the reactions were all stopped at a maximum conversion of 75% after four hours. In the vinyl acrylate used, the alcoholic leaving group is not stable, since vinyl alcohol isomerizes to acetaldehyde and the reaction equilibrium can thus no longer be shifted to the side of the reactants. Owing to their high preparation costs, such acrylic acid derivatives are not of interest for an economically viable synthesis.

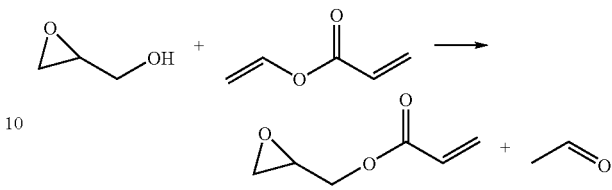

It was therefore an object of the present invention to provide a process with which (meth)acrylic esters of alcohols comprising epoxy groups can be obtained by (trans)esterification starting from (meth)acrylic and/or (meth)acrylic esters available on the industrial scale. The process should give rise to purities of at least >99% without complicated purification steps such as extraction or distillation of the product.

The object is achieved by a process for preparing (meth)acrylic esters (F) of alcohols (A) having at least one epoxy group, in which at least one alcohol (A) having at least one epoxy group is esterified with (meth)acrylic acid (S) or is transesterified with at least one (meth)acrylic ester (D) in the presence of at least one enzyme (E), the alcoholic leaving group being stable under the reaction conditions in the case of the transesterification.

Hereinafter, the reactants (meth)acrylic acid (S) and (meth)acrylic ester (D) are also summarized together under the term (meth)acrylic compound (B).

With the aid of the process according to the invention, the preparation of such (meth)acrylic esters (F) is possible in high chemical and space-time yield and under mild conditions with good color numbers, dispensing with protecting group operations and using simple starting materials.

The enzymatically catalyzed preparation of (meth)acrylic esters (F) comprising epoxy groups is effected under milder reaction conditions than with chemical esterification catalysts known from the prior art.

Alcohols (A) suitable in accordance with the invention are those alcohols which comprise at least one epoxy group and at least one hydroxyl group.

For example, such alcohols may comprise from 1 to 3, preferably from 1 to 2, epoxy groups, and more preferably exactly one epoxy group.

The alcohols (A) may comprise from one to six, preferably from one to four, more preferably from one to three, most preferably from one to two, hydroxyl groups, and especially exactly one hydroxyl group.

Particular preference is given to those alcohols (A) which comprise exactly one epoxy group and exactly one hydroxyl group.

The alcohols (A) usable in accordance with the invention may also comprise other heteroatoms, for example nitrogen, oxygen and sulfur; they are preferably formed only from carbon, hydrogen and oxygen atoms.

The alcohols (A) usable in accordance with the invention may also comprise other functional groups, for example C—C double bonds, amino, carboxyl, ether or carboxylic ester groups.

The hydroxyl groups of the alcohols (A) usable in accordance with the invention may be primary, secondary or tertiary; preference is given to those having primary or secondary hydroxyl groups and particular preference to those having primary hydroxyl groups.

Primary hydroxyl groups are hydroxyl groups which are bonded to a carbon atom which is bonded to exactly one further carbon atom. Analogously, in the case of secondary hydroxyl groups, the carbon atom bonded thereto is correspondingly bonded to two carbon atoms, and, in the case of tertiary hydroxyl groups, to three carbon atoms.

Preferred alcohols (A) are primary alcohols of the formula (1)

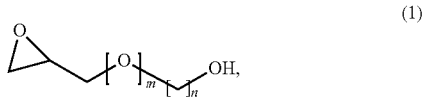

in which m is an integer and is 0 or 1 and n is likewise an integer of from 0 to 10, preferably from 1 to 8, more preferably from 1 to 6 and especially preferably from 1 to 4, with the proviso that, in the case that m=1, n≠0.

Examples of primary alcohols of the formula (1) are 2,3-epoxy-1-propanol (glycidol), 3,4-epoxy-1-butanol, 4,5-epoxy-1-pentanol, 5,6-epoxy-1-hexanol, hydroxyethyl glycidyl ether, hydroxypropyl glycidyl ether, hydroxybutyl glycidyl ether and hydroxypentyl glycidyl ether. In the case that n≧5, the alkyl radicals may also be branched, with the prerequisite that the hydroxyl group is a primary hydroxyl group.

Preferred alcohols (A) are 2,3-epoxy-1-propanol (glycidol), hydroxyethyl glycidyl ether and hydroxybutyl glycidyl ether.

When the alcohols (A) mentioned are optically active, they are preferably used in racemic form or as diastereomer mixtures, but it is also possible to use them as pure enantiomers or diastereomers or as enantiomer mixtures.

In the reaction step, the esterification with (meth)acrylic acid (S) or preferably the transesterification of the alcohol (A) with at least one (meth)acrylic ester (D) is effected in the presence of at least one enzyme (E), preferably of an enzyme (E) which catalyzes the transesterification.

In the case of transesterification, it is crucial that the alcoholic leaving group which is eliminated in the transesterification of the (meth)acrylic ester (D) is stable under the reaction conditions and, for example, does not isomerize. The reaction equilibrium can therefore also be shifted to the side of the reactants. Such (meth)acrylic esters (D) are described hereinafter, for example esters of saturated alcohols.

(Meth)acrylic acid (S) may be used for the esterification, or (meth)acrylic esters (D) of a saturated alcohol for the transesterification, preferably saturated $C_1$-$C_{10}$-alkyl esters or $C_3$-$C_{12}$-cycloalkyl esters of (meth)acrylic acid, more preferably saturated $C_1$-$C_4$-alkyl esters of (meth)acrylic acid.

In the context of this document, saturated means compounds without C—C multiple bonds (except, of course, the C=C double bond in the (meth)acryloyl units).

Examples of (meth)acrylic esters (D) are methyl (meth)acrylate, ethyl (meth)acrylate, n-butyl (meth)acrylate, isobutyl (meth)acrylate, n-octyl (meth)acrylate and 2-ethylhexyl (meth)acrylate, 1,2-ethylene glycol di- and mono(meth)acrylate, 1,4-butanediol di- and mono(meth)acrylate, 1,6-hexanediol di- and mono(meth)acrylate, trimethylolpropane tri(meth)acrylate and pentaerythritol tetra(meth)acrylate.

Particular preference is given to methyl (meth)acrylate, ethyl (meth)acrylate, n-butyl (meth)acrylate and 2-ethylhexyl (meth)acrylate.

Enzymes (E) usable in accordance with the invention are, for example, selected from hydrolases (E.C. 3.-.-.-), and among these particularly from the esterases (E.C. 3.1.-.-), lipases (E.C. 3.1.1.3), glycosylases (E.C. 3.2.-.-) and proteases (E.C. 3.4.-.-), in free form or in chemically or physically immobilized form on a support, preferably lipases, esterases or proteases and more preferably esterases (E.C. 3.1.-.-). Very particular preference is given to Novozyme® 435 (lipase from *Candida antarctica* B) or lipase from *Alcaligenes* sp., *Aspergillus* sp., *Mucor* sp., *Penicilium* sp., *Geotricum* sp., *Rhizopus* sp., *Burkholderia* sp., *Candida* sp., *Pseudomonas* sp., *Thermomyces* sp. or porcine pancreas; especially preferred lipases are those from *Candida antarctica* B or from *Burkholderia* sp.

The enzyme content in the reaction medium is generally in the range from about 0.1 to 10% by weight, based on the alcohol (A) used.

The enzymatic (trans)esterification of (meth)acrylic acid (S) or of (meth)acrylic esters (D) is effected generally at from 0 to 100° C., preferably from 20 to 80° C., more preferably from 20 to 70° C., most preferably from 20 to 60° C.

The reaction time depends on factors including the temperature, the amount used and the activity of the enzyme catalyst, and on the required conversion, and also on the alcohol. The reaction time is preferably adjusted such that the conversion of the hydroxyl functions which are to be converted and are present in the alcohol (A), i.e. those with a lower degree of substitution, is at least 70%, preferably at least 80%, more preferably at least 90%, even more preferably at least 95%, in particular at least 97% and especially at least 98%. In general, from 1 to 72 hours, preferably from 3 to 36 hours and more preferably from 3 to 24 hours are sufficient for this purpose.

The molar ratio of (meth)acrylic acid compound (B) (based on the (meth)acryloyl units) to alcohol (A) (based on the hydroxyl groups) can be adjusted within a wide range, for example in a ratio of from 100:1 to 1:1, preferably from 50:1 to 1:1, more preferably from 20:1 to 1:1 and most preferably from 10:1 to 1:1.

The reaction can proceed in organic solvents or mixtures thereof or without addition of solvents. Preference is given to not adding any solvent. The mixtures are generally substantially anhydrous, i.e. below 10% by volume, preferably below 5% by volume, more preferably below 1 % by volume and most preferably below 0.5% by volume of water addition).

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, methyl tert-butyl ether, ethyl tert-butyl ether, $C_1$-$C_4$-alkylene carbonates, especially propylene carbonate, $C_3$-$C_6$-alkyl acetates, especially tert-butyl acetate, tetrahydrofuran, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and mono- or polyphasic mixtures thereof. It may be advantageous to remove water or alcohol released by means of a binary or ternary heteroazeotrope which boils as close as possible to the temperature optimum of the enzyme (A) used. The alcohol thus removed can then be removed by phase separation or membrane vapor separation.

Optionally, aqueous solvents can be added to the organic solvents, so that—depending on the organic solvent—mono- or polyphasic reaction solutions are formed. Examples of aqueous solvents are water and aqueous, dilute (for example from 10 to 100 mM) buffers, for example having a pH in the range from about 6 to 8, for example potassium phosphate or TRIS-HCl buffer.

The proportion of water in the reaction mixture is generally 0-10% by volume. The reactants are preferably used without pretreatment (drying, water doping).

The substrates are present in the reaction medium in dissolved form, suspended as solids or in an emulsion. The initial concentration of the reactants is preferably in the range of from about 0.1 to 20 mol/l, in particular at from 0.15 to 10 mol/l or from 0.2 to 5 mol/l.

The reaction may be effected continuously, for example in a tubular reactor or in a stirred reactor battery, or batchwise.

The reaction may be carried out in all reactors suitable for such a reaction. Such reactors are known to those skilled in the art. Preference is given to effecting the reaction in a stirred tank reactor or a fixed bed reactor.

To mix the reaction mixture, any methods may be used. Special stirring apparatus is not required. The reaction medium may be mono- or polyphasic and the reactants are dissolved, suspended or emulsified therein, if appropriate initially charged together with the molecular sieve and admixed with the enzyme preparation at the start of the reaction, and also if appropriate once or more in the course of the reaction. The temperature is set to the desired value during the reaction and may, if desired, be increased or reduced during the course of the reaction.

When the reaction is carried out in a fixed bed reactor, the fixed bed reactor is preferably charged with immobilized enzymes, and the reaction mixture is pumped through a column filled with the enzyme. It is also possible to carry out the reaction in a fluidized bed, in which case the enzyme is used immobilized on a support. The reaction mixture may be pumped continuously through the column, and the flow rate can be used to control the residence time and thus the desired conversion. It is also possible to pump the reaction mixture in circulation through a column, in the course of which the alcohol released may also simultaneously be distilled off under reduced pressure.

The removal of water in the case of an esterification or alcohols which are released from the alkyl (meth)acrylates in a transesterification is effected continuously or stepwise in a manner known per se, for example by distillation, reduced pressure, azeotropic removal, absorption, pervaporation and diffusion through membranes.

Suitable methods for this purpose are preferably molecular sieves or zeolites (pore size, for example, in the range of about 3-10 ångström), a removal by distillation or with the aid of suitable semipermeable membranes.

However, it is also possible to feed the removed mixture of alkyl (meth)acrylate and the parent alcohol thereof, which frequently forms an azeotrope, directly into a plant for preparing the alkyl (meth)acrylate, in order to reutilize it there in an esterification with (meth)acrylic acid.

On completion of the reaction, the reaction mixture obtained from the (trans)esterification may be reused without further purification or it may, if required, be purified in a further step.

In general, in a purification step, only the enzyme used is removed from the reaction mixture, and the reaction product is removed from any organic solvent used.

A removal from the enzyme is effected generally by filtration, absorption, centrifugation or decanting. The removed enzyme may subsequently be used for further reactions.

The removal from the organic solvent is effected generally by distillation, rectification or, in the case of solid reaction products, by filtration.

For the further purification of the reaction product, chromatography may also be carried out.

However, preference is given in the purification step to removing only the enzyme and any solvent or the excess of (meth)acrylic acid or (meth)acrylate used.

The reaction conditions in the enzymatic (trans)esterification are mild. Owing to the low temperatures and otherwise mild conditions, the formation of by-products during the reaction is prevented, which can otherwise stem, for example, from chemical catalysts or as a result of undesired free-radical polymerization of the (meth)acrylate used, which can otherwise be prevented only by adding stabilizers.

In the inventive reaction, additional stabilizers may be added to the (meth)acrylic compound (B) over and above the storage stabilizer present in any case, for example hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2,2,6,6-tetramethylpiperidine N-oxyl, for example in amounts of from 50 to 2000 ppm. Advantageously, the (trans)esterification is carried out in the presence of an oxygenous gas, preferably air or air-nitrogen mixtures.

In addition, the enzyme catalyst can be removed in an unproblematic manner from the end product.

The reaction mixture can, if appropriate, be purified if desired, for example by filtration, distillation, rectification, chromatography, treatment with ion exchangers, adsorbents, neutral, acidic and/or alkaline washing, stripping or crystallization.

The present invention further provides the (meth)acrylic esters (F) obtained from the alcohols (A) by enzymatic (trans) esterification. As a result of the inventive reaction conditions, these have a color number below 100 APHA to DIN ISO 6271, preferably below 80. In addition, they comprise generally less than 1.0% by-products from rearrangement reactions of the double bond from acid- or base-catalyzed side reactions.

The advantage of the (meth)acrylic esters (F) obtained by the process according to the invention is that they can be used advantageously in coating applications owing to their low color number, especially in clearcoats, since they bring about reduced discoloration of the coatings compared to acrylates prepared by conventional processes owing to their low intrinsic color.

In addition, coatings comprising the (meth)acrylic esters (F) prepared in accordance with the invention have very high scratch resistances, hardnesses, chemical resistances, elasticity and adhesion, both on hydrophilic and on hydrophobic substrates.

The (meth)acrylic esters (F) obtainable in accordance with the invention may be used advantageously as monomers or comonomers in poly(meth)acrylates or as reactive diluents in thermally curable, radiation-curable and/or dual-curable poly (meth)acrylates. Such poly(meth)acrylates are, for example, suitable as binders in thermally curable, radiation-curable or dual-curable coating compositions, and also in adhesives, for example in acrylate adhesives, and also in sealant compositions.

The present application therefore further provides for the use of the (meth)acrylic esters (F) prepared by the process according to the invention as reactive diluents or binders in radiation-curable or dual-curable coating compositions, preferably in topcoats, more preferably in transparent clearcoats. It will be appreciated that the (meth)acrylic esters (F) prepared in accordance with the invention may also be used as monomers in polymerizations, if appropriate together with other polymerizable monomers, for example (meth)acrylic acid, (meth)acrylic esters, styrene, butadiene, acrylonitrile, vinyl acetate, N-vinylpyrrolidone, 4-hydroxybutyl vinyl ether or N-vinylformamide.

"Dual-cure" is understood to mean that the coatings are curable thermally and with actinic radiation. In the context of the present invention, actinic radiation is understood to mean electromagnetic radiation, such as visible light, UV radiation or X-radiation, especially UV radiation, and corpuscular radiation such as electron beams.

Radiation-curable binders are those which are curable by means of actinic radiation as defined above, especially by means of UV radiation.

The present application further provides coating formulations comprising the (meth)acrylic esters (F) obtainable by the process according to the invention. The (meth)acrylic esters (F) may be used both in basecoats and in topcoats. Owing to their particular properties, especially their low color number, their use in topcoats and radiation-cured clearcoats is preferred.

In addition to the (meth)acrylic esters (F) obtainable by the process according to the invention, an inventive radiation-curable composition may also comprise the following components:
(G) at least one polymerizable compound having a plurality of copolymerizable, ethylenically unsaturated groups,
(H) if appropriate reactive diluents,
(I) if appropriate photoinitiators and
(J) if appropriate further additives typical for coatings.

Useful compounds (G) include radiation-curable, free-radically polymerizable compounds having a plurality of, i.e. at least two, copolymerizable, ethylenically unsaturated groups.

Useful reactive diluents (compounds (H)) include radiation-curable, free-radically or cationically polymerizable compounds having only one ethylenically unsaturated, copolymerizable group.

The photoinitiators (I) used may be photoinitiators known to those skilled in the art, for example those mentioned in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (Eds), SITA Technology Ltd, London.

The further additives (J) typical for coatings which are used may, for example, be antioxidants, oxidation inhibitors, stabilizers, activators (accelerants), fillers, pigments, dyes, devolatilizers, luster agents, antistats, flame retardants, thickeners, thixotropic agents, leveling agents, binders, antifoams, fragrances, surfactants, viscosity modifiers, plasticizers, tackifying resins (tackifiers), chelating agents or compatibilizers.

Examples of the compound classes (G), (H), (I) and (J) mentioned are disclosed in WO 2006/005491 and in the German application with the reference number DE 10 2005 037 430.1 which was unpublished at the priority date of the present application. Reference is made explicitly at this point to both of these documents.

Typical compositions for radiation-curable compositions are, for example,
(F) 20-100% by weight, preferably 40-90% by weight, more preferably 50-90% by weight and in particular 60-80% by weight,
(G) 0-60% by weight, preferably 5-50% by weight, more preferably 10-40% by weight and in particular 10-30% by weight,
(H) 0-50% by weight, preferably 5-40% by weight, more preferably 6-30% by weight and in particular 10-30% by weight,
(I) 0-20% by weight, preferably 0.5-15% by weight, more preferably 1-10% by weight and in particular 2-5% by weight and
(J) 0-50% by weight, preferably 2-40% by weight, more preferably 3-30% by weight and in particular 5-20% by weight,
with the proviso that (F), (G), (H), (I) and (J) together add up to 100% by weight.

The substrates are coated by customary processes known to those skilled in the art, where at least one coating composition is applied to the substrate to be coated in the desired thickness, and any volatile constituents present in the coating composition, if appropriate after heating, are removed. This operation can be repeated once or more than once if desired. The application to the substrate can be effected in a known manner, for example by spraying, troweling, knifecoating, brushing, rolling, roller coating, casting, laminating, injection backmolding or coextrusion. The coating thickness is generally within a range from about 3 to 1000 g/m$^2$ and preferably from 10 to 200 g/m$^2$.

In addition, a process for coating substrates is disclosed, in which the coating composition is applied to the substrate and dried if appropriate, cured with electron beams or UV illumination under an oxygenous atmosphere or preferably under inert gas, if appropriate at temperatures up to the magnitude of the drying temperature.

In addition to or instead of the thermal drying, the drying can also be effected by NIR radiation, NIR radiation referring here to electromagnetic radiation in the wavelength range from 760 nm to 2.5 µm, preferably from 900 to 1500 nm.

If appropriate, when a plurality of layers of the coating composition are applied one on top of another, a thermal and/or NIR drying and radiative curing can be effected after each coating operation.

Suitable radiation sources for the radiative curing are, for example, low-pressure, medium-pressure and high-pressure mercury lamps, and luminescent tubes, pulsed lamps, metal halide lamps, electron flash installations, which allow radiative curing without photoinitiator, or excimer lamps. The radiative curing is effected by the action of high-energy radiation, i.e. UV radiation or daylight, preferably light in the wavelength range of $\lambda$=from 200 to 700 nm, more preferably of $\lambda$=from 200 to 500 nm and most preferably $\lambda$=from 250 to 400 nm, or by irradiation with high-energy electrons (electron radiation; from 150 to 300 keV). The radiation sources used are, for example, high-pressure mercury vapor lamps, lasers, pulsed lamps (flash light), halogen lamps or excimer lamps. The radiation dose typically sufficient for crosslinking in the case of UV curing is in the range from 80 to 3000 mJ/cm$^2$.

It is of course also possible to use a plurality of radiation sources for the curing, for example from two to four. These may also radiate in different wavelength ranges in each case.

The irradiation can, if appropriate, also be performed with exclusion of oxygen, for example under inert gas atmosphere. Suitable inert gases are preferably nitrogen, noble gases, carbon dioxide, or combustion gases. In addition, the irradiation can be effected by covering the coating composition with transparent media. Transparent media are, for example, polymer films, glass or liquids, for example water. Particular preference is given to irradiation in the manner as described in DE 199 57 900 A1.

Substrates coated with an inventive multilayer coating also form part of the subject matter of the present invention.

The thickness of a layer to be cured as described may be from 0.1 µm to several mm, preferably from 1 to 2000 µm, more preferably from 5 to 1000 µm, even more preferably from 10 to 500 µm and in particular from 10 to 250 µm.

Owing to their low discoloration, the (meth)acrylic esters (F) prepared in accordance with the invention can advantageously also be used in a thermally induced (free-radical) (co)polymerization.

Examples of monomers with which the (meth)acrylic esters (F) prepared in accordance with the invention can be copolymerized, for example, include $C_1$-$C_{20}$-alkyl (meth)acrylates, vinylaromatic having up to 20 carbon atoms, vinyl esters of carboxylic acids comprising up to 20 carbon atoms, ethylenically unsaturated nitriles, vinyl ethers of alcohols comprising from 1 to 10 carbon atoms, and aliphatic hydrocarbons having from 2 to 8 carbon atoms and 1 or 2 double bonds.

Preferred alkyl (meth)acrylates are those having a $C_1$-$C_{10}$-alkyl radical, such as methyl methacrylate, methyl acrylate, n-butyl acrylate, ethyl acrylate and branched alkyl derivatives such as 2-ethylhexyl acrylate.

In particular, mixtures of the alkyl (meth)acrylates are also suitable.

Vinyl esters of carboxylic acids having from 1 to 20 carbon atoms are, for example, vinyl laurate, vinyl stearate, vinyl propionate and vinyl acetate.

Useful vinylaromatic compounds include, for example, vinyltoluene, a-butylstyrene, 4-n-butylstyrene, 4-n-decylstyrene and preferably styrene.

Examples of nitriles are acrylonitrile and methacrylonitrile.

Suitable vinyl ethers are, for example, vinyl methyl ether, vinyl isobutyl ether, vinyl hexyl ether and vinyl octyl ether.

Nonaromatic hydrocarbons having from 2 to 8 carbon atoms and one or two olefinic double bonds include butadiene, isoprene, and also ethylene, propylene and isobutylene.

A frequent method, but not the only method, for preparing such (co)polymers is free-radical or ionic (co)polymerization in a solvent or diluent.

The free-radical (co)polymerization of such monomers is effected, for example, in aqueous solution in the presence of polymerization initiators which decompose into free radicals under polymerization conditions, for example peroxodisulfates, $H_2O_2$ redox systems or hydroperoxides, for example tert-butyl hydroperoxide or cumene hydroperoxide. The (co)polymerization can be undertaken within a wide temperature range, if appropriate under reduced pressure or else under elevated pressure, generally at temperatures up to 100° C. The pH of the reaction mixture is commonly adjusted within the range from 4 to 10.

The (co)polymerization can also be performed continuously or batchwise in another manner known per se to those skilled in the art, for example as a solution polymerization, precipitation polymerization, water-in-oil emulsion polymerization, inverse emulsion polymerization, suspension polymerization or inverse suspension polymerization.

The monomer/the monomers are (co)polymerized using free-radical polymerization initiators, for example azo compounds which decompose into free radicals, such as 2,2'-azobis(isobutyronitrile), 2,2'-azobis(2-amidinopropane) hydrochloride or 4,4'-azobis (4'-cyanopentanoic acid), or dialkyl peroxides such as di-tert-amyl peroxide, aryl alkyl peroxides such as tert-butyl cumyl peroxide, alkyl acyl peroxide such as tert-butyl peroxy-2-ethylhexanoate, peroxydicarbonates such as di(4-tert-butylcyclohexyl) peroxydicarbonate, or hydroperoxides.

The compounds mentioned are usually used in the form of aqueous solutions or aqueous emulsions, the lower concentration being determined by the amount of water acceptable in the (co)polymerization and the upper concentration by the solubility of the compound in question in water.

The solvents or diluents used may, for example, be water, alcohols such as methanol, ethanol, n- or isopropanol, n- or isobutanol, or ketones such as acetone, ethyl methyl ketone, diethyl ketone or isobutyl methyl ketone. Particular preference is given to nonpolar solvents, for example xylene and isomer mixtures thereof, Shellsol® A and Solvent Naphtha.

In a preferred embodiment, the monomers are premixed, and initiator is added dissolved in solvent with any further additives. A particularly preferred embodiment is described in WO 2001/23484 and there particularly on page 10 line 3 to line 24.

If appropriate, the (co)polymerization can be performed in the presence of polymerization regulators, for example hydroxyl ammonium salts, chlorinated hydrocarbons and thio compounds, for example tert-butyl mercaptan, ethylacryloyl thioglycolate, mercaptoethynol, mercaptopropyltrimethoxysilane, dodecyl mercaptan, tert-dodecyl mercaptan or alkali metal hypophosphites. In the (co)polymerization, these regulators may be used, for example, in amounts of from 0 to 0.8 part by weight, based on 100 parts by weight of the monomers to be (co)polymerized, by virtue of which the molar mass of the (co)polymer formed is reduced.

In the emulsion polymerization, dispersants, ionic and/or nonionic emulsifiers and/or protective colloids or stabilizers may be used as interface-active compounds. Useful such compounds include both protective colloids typically used to perform emulsion polymerizations and emulsifiers.

Suitable protective colloids are, for example, polyvinyl alcohols, cellulose derivatives or copolymers comprising vinylpyrrolidone. A comprehensive description of further suitable protective colloids can be found in Houben-Weyl, Methoden der organischen Chemie [Methods of Organic Chemistry], Volume XIV/1, makromolekulare Stoffe [Macromolecular substances], Georg-Thieme-Verlag, Stuttgart, 1969, p. 411 to 420. It is of course also possible to use mixtures of emulsifiers and/or protective colloids. The dispersants used are preferably exclusively emulsifiers whose relative molecular weights, in contrast to the protective colloids, are typically below 1000. They may be of anionic, cationic or nonionic nature. Of course, in the case of use of mixtures of interface-active substances, the individual components have to be compatible with one another, which can be checked in the case of doubt with the aid of a few preliminary experiments. In general, anionic emulsifiers are compatible with one another and with nonionic emulsifiers.

The same also applies to cationic emulsifiers, while anionic and cationic emulsifiers are usually incompatible with one another. Commonly used emulsifiers are, for example, ethoxylated mono-, di- and trialkylphenols (EO: 3 to 100, alkyl radical: $C_4$ to $C_{12}$), ethoxylated fatty alcohols (EO: 3 to 100, alkyl radical: $C_8$ to $C_{18}$), and alkali metal and ammonium salts of alkyl sulfates (alkyl radical: $C_8$ to $C_{16}$) of sulfuric monoesters of ethoxylated alkylphenols (EO: 3 to 100, alkyl radical: $C_4$ to $C_{12}$), of alkylsulfonic acids (alkyl radical: $C_{12}$ to $C_{18}$) and of alkylacryloylsulfonic acids (alkyl radical: $C_9$ to $C_{18}$). Further suitable emulsifiers such as sulfosuccinic esters can be found in Houben-Weyl, Methoden der organischen Chemie, Volume XIV/1, Makromolekulare Stoffe, Georg-Thieme Verlag, Stuttgart, 1961, pages 192 to 208.

In general, the amount of dispersant used is from 0.5 to 6% by weight, preferably from 1 to 3% by weight, based on the monomers to be polymerized by free-radical means.

Examples of (meth)acrylate-containing dispersions are n-butyl acrylate/acrylonitrile dispersions which find use as adhesives, and also n-butyl acrylate/butadiene/styrene dispersions.

The polymer dispersions in which (meth)acrylic esters (F) prepared in accordance with the invention are used may additionally be chemically and/or physically deodorized.

A chemical deodorization can be performed, for example, as described by P. H. H. Araujo, C. Sayer, J. G. R. Poco, R. Giudici, in Polymer Engineering and Science, 2002 (42), 1442-1468 or as disclosed in EP 1 375 530 B1.

The copolymers obtainable with the (meth)acrylic esters (F) prepared in accordance with the invention generally have a relatively low color number, which is advantageous in the coatings sector. The copolymers described can then be reacted in a manner known per se, for example with amino resins, for example melamine, to give crosslinked coating resins, as described, for example, in EP 0 738 740 or EP 0 675 141.

The inventive coating compositions are more preferably suitable as or in exterior coatings, i.e. those applications which are exposed to daylight, preferably of buildings or building parts, interior coatings, road markings, coatings on vehicles and aeroplanes. In particular, the coatings are used as wood, paper or plastic coatings, for example for parquet or furniture.

The invention further provides for the use of the products obtained in accordance with the invention as a precursor for luster additives in electroplating. Their reduced color number compared to products obtainable conventionally makes them exceptionally suitable for this use.

With the aid of the process according to the invention, the preparation of (meth)acrylic esters (F) is possible in high chemical and space-time yield and under mild conditions with good color numbers. In spite of activated (meth)acrylic acid compounds being dispensed with, the desired products are obtained with high selectivity in a controlled manner, and are substantially free of by-products.

The examples which follow are intended to illustrate the properties of the invention, but without restricting them.

EXAMPLES

In this document, unless stated otherwise, "parts" are understood to mean "parts by weight".

Example 1

Preparation of Glycidol Acrylate in Solvent

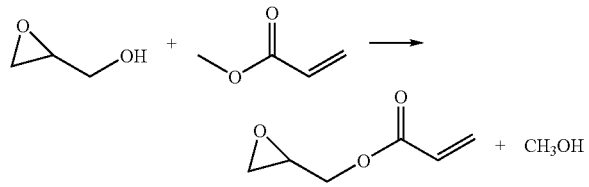

In a screw-top glass container, in each case 5 mMol of glycidol (370 mg) were agitated with 10 or 50 mMol of methyl acrylate, 50 mg of Novozym® 435 (supported lipase from *Candida antarctica* B, from Novozymes, Denmark), 5.0 ml of MTBE (tert-butyl methyl ether) and, in some cases, 1.0 g of 5 Å molecular sieve at 20 or 40° C. for 24 h. Thereafter, the enzyme was filtered off and the excess of methyl acrylate was removed on a rotary evaporator. A colorless acrylate was obtained.

To determine the conversion, a sample was silylated and the conversion from alcohol to acrylate was determined by means of GC. No by-products having a content of >0.2% were found.

Conversions [%] at 20° C.

| Methacrylate [mmol] | Without MS | With MS |
|---|---|---|
| 10 | 47 | 70 |
| 50 | 74 | 92 |
| 50 | — | 64 |

* MS = 5 Å molecular sieve
[a] With lipase from *Burkholderia plantarii* instead of Novozym® 435

Conversions [%] at 40° C.

| Methacrylate [mmol] | Without MS | With MS |
|---|---|---|
| 10 | 49 | 79 |
| 50 | 76 | >99 |

* MS = 5 Å molecular sieve

Example 2

Preparation of 4-hydroxybutyl acrylate glycidyl ether (4-HBAGE) with Different Excess of Methyl Acrylate

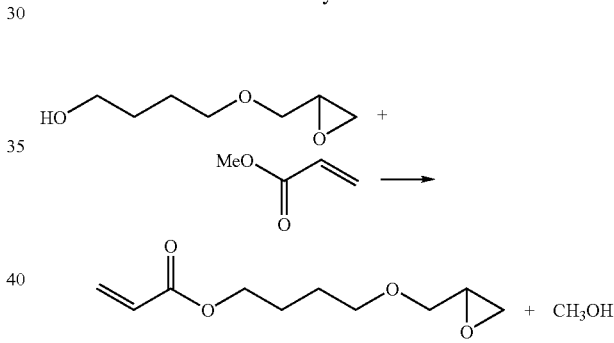

In a screw-top glass container, in each case 5 mMol of 4-hydroxybutyl glycidyl ether (731 mg) were agitated with 20, 30, 40 or 50 mMol of methyl acrylate, 0 or 25 mg of Novozym 435 (supported lipase from *Candida antarctica* B, from Novozymes, Denmark) and, in some cases, 1.0 g of 5 Å molecular sieve at 40° C. for 24 h. Thereafter, the enzyme was filtered off and the excess of methyl acrylate was removed on a rotary evaporator. A colorless acrylate was obtained.

To determine the conversion, a sample was silylated, and the conversion of alcohol to acrylate was determined by means of GC. No by-products having a content of >0.2% were found.

| Methyl acrylate [mmol] | Comment | Conversion [%] |
|---|---|---|
| 50 | without enzyme | 0 |
| 50 | without molecular sieve | 29 |
| 50 | — | 100 |
| 40 | — | 100 |
| 30 | — | 100 |
| 20 | — | 100 |

Example 3

Preparation of 4-hydroxybutyl acrylate glycidyl ether (4-HBAGE), Influence of Temperature and Reaction Time

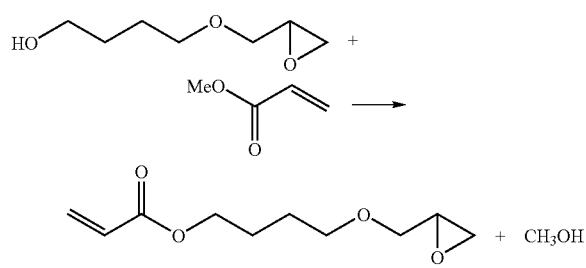

In each case 20 mMol of 4-hydroxybutyl glycidyl ether (2.92 g) were stirred with 80 mMol of methyl acrylate (6.89 g), 100 mg of Novozym® 435 and 4.0 g of 5 Å molecular sieve were stirred at 20 or 40° C. for 2, 4, 6, 8 or 24 h. Thereafter, the enzyme was filtered off and the excess of methyl acrylate was removed on a rotary evaporator. A colorless acrylate was obtained with 93% (at 20° C.) or 94% (at 40° C.) yield.

To determine the conversion, a sample was silylated in each case, and the conversion of alcohol to acrylate was determined by GC. No by-products having a content of >0.2% were found.

| Reaction time [h] | Conversion [%] at 20° C. | Conversion [%] at 40° C. |
|---|---|---|
| 2 | 16 | 45 |
| 4 | 33 | 78 |
| 6 | 49 | 97 |
| 8 | 62 | 100 |
| 24 | 100 | 100 |

The invention claimed is:

1. A process for preparing the compound of Formula (I):

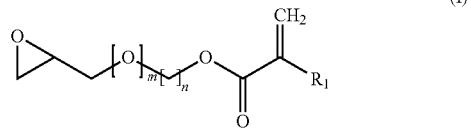 (I)

wherein $R_1$ is hydrogen or methyl, m is an integer from 0 to 1 and n is an integer from 0 to 10, with the proviso that in the case that m=0, n ≠0, comprising transesterifying the compound of Formula (II):

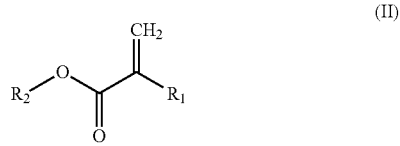 (II)

wherein $R_1$ is hydrogen or methyl and $R_2$ is a saturated alkyl group with the compound of Formula (III):

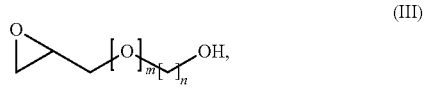 (III)

in the presence of a lipase to obtain the compound of formula (I).

2. The process according to claim 1, wherein the compound of formula (III) is selected from the group consisting of 2,3-epoxy-1-propanol, hydroxyethyl glycidyl ether and hydroxybuty glycidyl ether.

3. The process according to claim 1, wherein $R_2$ is a saturated $C_1$ to $C_{10}$ alkyl group.

4. The process according to claim 1, wherein the compound of formula (II) is selected from the group consisting of methyl (meth)acrylate, n-butyl (meth)acrylate and 2-ethylhexyl (meth) acrylate.

5. The process according to claim 1, wherein the reaction is conducted in a stirred tank reactor.

6. The process according to claim 1, wherein the reaction is conducted in a fixed bed reactor.

7. The process according to claim 1, wherein the lipase is present in an amount from about 0.1 to 10% by weight based on the compound of formula (II).

8. The process according to claim 1, wherein occurs at a temperature from 20 to 80 degrees C.

9. The process, according to claim 1, wherein the reaction occurs in the presence of an organic solvent or a mixture of organic solvents.

* * * * *